US012804316B2

(12) United States Patent
Kato et al.

(10) Patent No.: US 12,804,316 B2
(45) Date of Patent: Nov. 17, 2026

(54) BIOACOUSTIC SENSOR AND STETHOSCOPE INCLUDING THE SAME

(71) Applicant: Murata Manufacturing Co., Ltd., Nagaokakyo (JP)

(72) Inventors: Takatoshi Kato, Nagaokakyo (JP); Hirofumi Watanabe, Nagaokakyo (JP); Hironari Yamamoto, Nagaokakyo (JP); Koichi Inoue, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 77 days.

(21) Appl. No.: 18/797,710

(22) Filed: Aug. 8, 2024

(65) Prior Publication Data

US 2024/0397259 A1 Nov. 28, 2024

Related U.S. Application Data

(60) Division of application No. 17/751,793, filed on May 24, 2022, now Pat. No. 12,089,002, which is a (Continued)

(30) Foreign Application Priority Data

Nov. 29, 2019 (JP) ................................ 2019-216830

(51) Int. Cl.
*H04R 1/46* (2006.01)
*A61B 7/04* (2006.01)
(Continued)

(52) U.S. Cl.
CPC ................ *H04R 1/46* (2013.01); *A61B 7/04* (2013.01); *H04R 1/04* (2013.01); *H04R 1/1016* (2013.01);
(Continued)

(58) Field of Classification Search
CPC .......... H04R 1/46; H04R 1/04; H04R 1/1016; H04R 7/04; H04R 7/20; H04R 7/26;
(Continued)

(56) References Cited

U.S. PATENT DOCUMENTS 4,258,229 A * 3/1981 Eggert .................. H04R 17/02 381/67
8,447,043 B1 * 5/2013 Abbruscato ............. A61B 7/04 381/67
(Continued)

OTHER PUBLICATIONS

Kato et al., "Bioacoustic Sensor and Stethoscope Including the Same", U.S. Appl. No. 17/751,793, filed May 24, 2022.

*Primary Examiner* — Jason R Kurr
(74) *Attorney, Agent, or Firm* — Keating & Bennett, LLP

(57) ABSTRACT

A bioacoustic sensor includes a diaphragm including a contact surface contactable with a living body and a back surface, and being displaceable in a thickness direction, and a piezoelectric plate including a first surface facing the back surface of the diaphragm with a gap therebetween and a second surface on a side opposite to the first surface to convert the vibration of the diaphragm into an electric signal. The diaphragm is in contact with a center side portion of the first surface of the piezoelectric plate when viewed in the thickness direction, and a housing supports an outer side portion of the second surface of the piezoelectric plate when viewed in the thickness direction.

16 Claims, 9 Drawing Sheets

Related U.S. Application Data continuation of application No. PCT/JP2020/043661, filed on Nov. 24, 2020.

(51) Int. Cl.

| | |
|---|---|
| ***H04R 1/04*** | (2006.01) |
| ***H04R 1/10*** | (2006.01) |
| ***H04R 7/04*** | (2006.01) |
| ***H04R 7/20*** | (2006.01) |
| ***H04R 7/26*** | (2006.01) |
| ***H04R 17/02*** | (2006.01) |

(52) U.S. Cl.
CPC ................. *H04R 7/04* (2013.01); *H04R 7/20* (2013.01); *H04R 7/26* (2013.01); *H04R 17/02* (2013.01)

(58) Field of Classification Search
CPC ........ H04R 17/02; H04R 17/025; A61B 7/02; A61B 7/04
USPC ............................................................ 381/67
See application file for complete search history.

(56) References Cited

U.S. PATENT DOCUMENTS

| | | | | |
|---|---|---|---|---|
| 12,089,002 | B2 * | 9/2024 | Kato | H04R 7/26 |
| 2008/0137876 | A1 * | 6/2008 | Kassal | A61B 7/04 381/67 |
| 2018/0324530 | A1 * | 11/2018 | Hoskins | H04R 17/02 |

* cited by examiner

BIOACOUSTIC SENSOR AND STETHOSCOPE INCLUDING THE SAME

CROSS REFERENCE TO RELATED APPLICATIONS

This application claims the benefit of priority to Japanese Patent Application No. 2019-216830 filed on Nov. 29, 2019 and is a Continuation Application of PCT Application No. PCT/JP2020/043661 filed on Nov. 24, 2020. The entire contents of each application are hereby incorporated herein by reference.

BACKGROUND OF THE INVENTION

1. Field of the Invention

The present invention relates to a bioacoustic sensor for measuring a sound generated by a living body such as a heart sound, and a stethoscope including the same.

2. Description of the Related Art

For example, Japanese Unexamined Patent Application Publication No. 2009-517129 discloses a bioacoustic sensor including a transducer element (piezoelectric plate) that is deformed and generates an electric signal corresponding to the deformation. In the bioacoustic sensor, the piezoelectric plate is attached in its entirety, with a fixing arrangement (adhesive) applied, to an inner side surface portion on the opposite side to an outer side surface portion of a housing in contact with a living body. With this, the piezoelectric plate receives a sound (vibration) generated by the living body via the housing, is deformed with the vibration, and generates an electric signal corresponding to a deformation amount.

SUMMARY OF THE INVENTION

However, in the case of the bioacoustic sensor described in Japanese Unexamined Patent Application Publication No. 2009-517129, the piezoelectric plate is attached in its entirety to the housing to be in contact with a living body. Because of the above, the deformation of the piezoelectric plate is limited by the housing. As a result, the bioacoustic sensor has low vibration detection sensitivity for the living body in contact with the housing.

Preferred embodiments of the present invention increase vibration detection sensitivity in a bioacoustic sensor using a piezoelectric plate.

According to an aspect of a preferred embodiment of the present invention, a bioacoustic sensor includes a housing, a diaphragm including a contact surface contactable with a living body and a back surface on an opposite side to the contact surface, and being displaceable in a thickness direction, and a piezoelectric plate including a first surface facing the back surface of the diaphragm with a gap between the first surface and the back surface and a second surface on an opposite side to the first surface to convert vibration of the diaphragm into an electric signal, wherein the diaphragm is in contact with a center side portion of the first surface of the piezoelectric plate when viewed in the thickness direction, and the housing supports an outer side portion of the second surface of the piezoelectric plate when viewed in the thickness direction.

Further, according to another aspect of a preferred embodiment of the present invention, there is provided a bioacoustic sensor including a housing, a diaphragm including a contact surface contactable with a living body and a back surface on an opposite side to the contact surface, and being displaceable in a thickness direction, and a piezoelectric plate including a first surface facing the back surface of the diaphragm with a gap between the first surface and the back surface and a second surface on an opposite side to the first surface to convert vibration of the diaphragm into an electric signal, wherein the diaphragm is in contact with an outer side portion of the first surface of the piezoelectric plate when viewed in the thickness direction, and the housing supports a center side portion of the second surface of the piezoelectric plate when viewed in the thickness direction.

Further, according to still another aspect of a preferred embodiment of the present invention, a stethoscope includes the bioacoustic sensor, a speaker drivable based on an electric signal from the piezoelectric plate of the bioacoustic sensor, a chest piece including the bioacoustic sensor and the speaker, and an ear chip connected to the chest piece to output a sound of the speaker to outside.

According to preferred embodiments of the present invention, vibration detection sensitivity may be increased in a bioacoustic sensor using a piezoelectric plate.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
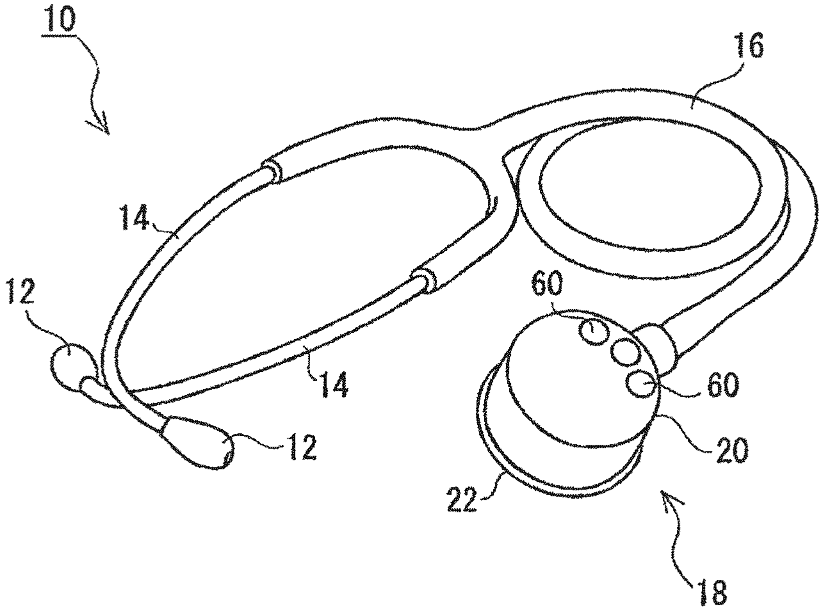
FIG. 1 is a perspective view of a stethoscope including a bioacoustic sensor according to Preferred Embodiment 1 of the present invention.

A bioacoustic sensor according to an aspect of a preferred embodiment of the present invention includes a housing, a diaphragm including a contact surface contactable with a living body and a back surface on an opposite side to the contact surface, and being displaceable in a thickness direction, and a piezoelectric plate including a first surface facing the back surface of the diaphragm with a gap therebetween and a second surface on an opposite side to the first surface to convert vibration of the diaphragm into an electric signal. The diaphragm is in contact with a center side portion of the first surface of the piezoelectric plate when viewed in the thickness direction, and the housing supports an outer side portion of the second surface of the piezoelectric plate when viewed in the thickness direction.

According to the aspect above, in a bioacoustic sensor including a piezoelectric plate, the vibration detection sensitivity may be increased.

For example, the bioacoustic sensor may further include a diaphragm support provided to the housing to support the diaphragm, and is elastically deformable in the thickness direction. With this, the diaphragm may be displaced in the thickness direction thereof.

For example, a portion of the housing facing the second surface of the piezoelectric plate may include a concave surface, and the housing may directly support the outer side portion of the second surface of the piezoelectric plate via the concave surface. When excessive force is applied to the diaphragm, the entire piezoelectric plate is brought into contact with the concave surface of the housing. This makes it possible to reduce or prevent damage due to excessive flexural deformation of the piezoelectric plate.

For example, a convex surface corresponding to the concave surface of the housing may be provided to the back surface of the diaphragm and the diaphragm may be in direct contact with the piezoelectric plate via the convex surface. When excessive force is applied to the diaphragm, the entire piezoelectric plate is sandwiched and held between the concave surface of the housing and the convex surface of the diaphragm. This makes it possible to reduce or prevent damage due to the excessive flexural deformation of the piezoelectric plate.

For example, the bioacoustic sensor may further include a vibration transmitter and a piezoelectric plate support as follows. The vibration transmitter is sandwiched between the diaphragm and the piezoelectric plate and is in contact with the center side portion of the first surface of the piezoelectric plate to transmit vibration of the diaphragm to the piezoelectric plate. The piezoelectric plate support is sandwiched between the piezoelectric plate and the housing to support the outer side portion of the second surface of the piezoelectric plate. In the case above, the diaphragm is in indirect contact with the piezoelectric plate via the vibration transmitter, and the housing indirectly supports the piezoelectric plate via the piezoelectric plate support.

For example, a thickness of the piezoelectric plate support may be a thickness with which the center of the second surface of the piezoelectric plate comes into contact with the housing, when a predetermined force or more is applied to the diaphragm and the piezoelectric plate is flexurally deformed. With this, damage due to the excessive flexural deformation of the piezoelectric plate may be reduced or prevented.

For example, a thickness of the vibration transmitter may be a thickness with which an outer peripheral edge of the first surface of the piezoelectric plate comes into contact with the diaphragm when a predetermined force or more is applied to the diaphragm and the piezoelectric plate is flexurally deformed. With this, damage due to the excessive flexural deformation of the piezoelectric plate may be reduced or prevented.

For example, the piezoelectric plate support may be made of an elastically deformable material. With this, the piezoelectric plate support defines and functions as a damper and may absorb high frequency components of an undesirable vibration.

For example, the vibration transmitter may include a columnar body, and the piezoelectric plate support may include an annular body along the outer peripheral edge of the piezoelectric plate.

For example, one end surface of the vibration transmitter may be fixed to the back surface of the diaphragm.

For example, another end surface of the vibration transmitter may be fixed to the first surface of the piezoelectric plate.

For example, the vibration transmitter may have a lower hardness in an outer side portion than in a center side portion. With this, stress concentration in a portion of the piezoelectric plate in contact with the corner of the end surface of the vibration transmitter is alleviated thus preventing or reducing damage to the piezoelectric plate.

For example, the end surface of the vibration transmitter on the side of the piezoelectric plate may include a rounded corner. With this, the stress concentration on the piezoelectric plate is alleviated in comparison with a case that the end surface has a sharp corner, thus reducing or preventing damage to the piezoelectric plate.

For example, the bioacoustic sensor may further include a first damper between the diaphragm and the piezoelectric plate, and a second damper between the piezoelectric plate and the housing. In the case above, the first damper has a hardness lower than that of the vibration transmitter, and the second damper has a hardness lower than that of the piezoelectric plate support. With this, contact between the diaphragm and the piezoelectric plate and contact between the piezoelectric plate and the housing are reduced or prevented.

A bioacoustic sensor according to another aspect of a preferred embodiment of the present invention includes a housing, a diaphragm including a contact surface contactable with a living body and a back surface on an opposite side to the contact surface, and being displaceable in a thickness direction, and a piezoelectric plate including a first surface facing the back surface of the diaphragm with a gap therebetween and a second surface on an opposite side to the first surface to convert vibration of the diaphragm into an electric signal. The diaphragm is in contact with an outer side portion of the first surface of the piezoelectric plate when viewed in the thickness direction, and the housing supports a center side portion of the second surface of the piezoelectric plate when viewed in the thickness direction.

According to the aspect above, in a bioacoustic sensor including a piezoelectric plate, the vibration detection sensitivity may be increased.

For example, the bioacoustic sensor may further include a diaphragm support provided to the housing to support the diaphragm, and is elastically deformable in the thickness direction. With this, the diaphragm may be displaced in the thickness direction thereof.

For example, the back surface of the diaphragm may include a concave surface and the diaphragm may be in direct contact with the outer side portion of the first surface of the piezoelectric plate via the concave surface. When excessive force is applied to the diaphragm, the entire piezoelectric plate is brought into contact with the concave surface of the diaphragm. This makes it possible to reduce or prevent damage due to the excessive flexural deformation of the piezoelectric plate.

For example, a portion of the housing facing the second surface of the piezoelectric plate may include a convex surface corresponding to the concave surface of the diaphragm, and the housing may directly support the piezoelectric plate via the convex surface. When excessive force is applied to the diaphragm, the entire piezoelectric plate is sandwiched and held between the concave surface of the diaphragm and the convex surface of the housing. This makes it possible to reduce or prevent damage due to the excessive flexural deformation of the piezoelectric plate.

For example, the bioacoustic sensor may further include a vibration transmitter and a piezoelectric plate support as follows. The vibration transmitter is sandwiched between the diaphragm and the piezoelectric plate, and is in contact with the outer side portion of the first surface of the piezoelectric plate to transmit vibration of the diaphragm to the piezoelectric plate. The piezoelectric plate support is sandwiched between the piezoelectric plate and the housing to support the center side portion of the second surface of the piezoelectric plate. In the case above, the diaphragm indirect contact with the piezoelectric plate via the vibration transmitter, and the housing indirectly supports the piezoelectric plate via the piezoelectric plate support.

For example, the thickness of the vibration transmitter may be the thickness with which the center of the first surface of the piezoelectric plate comes into contact with the diaphragm when a predetermined force or more is applied to the diaphragm and the piezoelectric plate is flexurally deformed. With this, damage due to the excessive flexural deformation of the piezoelectric plate may be reduced or prevented.

For example, the thickness of the piezoelectric plate support may be the thickness with which the outer peripheral edge of the second surface of the piezoelectric plate comes into contact with the housing when a predetermined force or more is applied to the diaphragm and the piezoelectric plate is flexurally deformed. With this, damage due to the excessive flexural deformation of the piezoelectric plate may be reduced or prevented.

For example, the piezoelectric plate support may be made of an elastically deformable material. With this, the piezoelectric plate support defines and functions as a damper and may absorb the high frequency components of an undesirable vibration.

For example, the vibration transmitter may include an annular body along the outer peripheral edge of the piezoelectric plate, and the piezoelectric plate support may include a columnar body.

For example, one end surface of the vibration transmitter may be fixed to the back surface of the diaphragm.

For example, another end surface of the vibration transmitter may be fixed to the first surface of the piezoelectric plate.

For example, the bioacoustic sensor may further include a first damper between the diaphragm and the piezoelectric plate, and a second damper between the piezoelectric plate and the housing. In the case above, the first damper has a hardness lower than that of the vibration transmitter, and the second damper has a hardness lower than that of the piezoelectric plate support. With this, contact between the diaphragm and the piezoelectric plate and contact between the piezoelectric plate and the housing are reduced or prevented.

A stethoscope according to another aspect of a preferred embodiment of the present invention includes the bioacoustic sensor, a speaker to be driven based on an electric signal from the piezoelectric plate of the bioacoustic sensor, a chest piece including the bioacoustic sensor and the speaker, and an ear chip connected to the chest piece to output the sound of the speaker to the outside.

According to the aspect above, in a stethoscope including a bioacoustic sensor including a piezoelectric plate, vibration detection sensitivity, that is, for a sound, may be increased.

Hereinafter, preferred embodiments of the present invention will be described with reference to the drawings.

Preferred Embodiment 1

FIG. 1 is a perspective view of a stethoscope including a bioacoustic sensor according to Preferred Embodiment 1 of the present invention.

As illustrated in FIG. 1, a stethoscope 10 according to Preferred Embodiment 1 is a so-called digital stethoscope, and includes two ear tubes 14 each including an ear chip 12 attached to the distal end thereof, a Y-shaped tube 16 connected to the two ear tubes 14, and a chest piece 18 connected to the Y-shaped tube 16. The bioacoustic sensor according to Preferred Embodiment 1 is incorporated in the chest piece 18.

Figure 2:
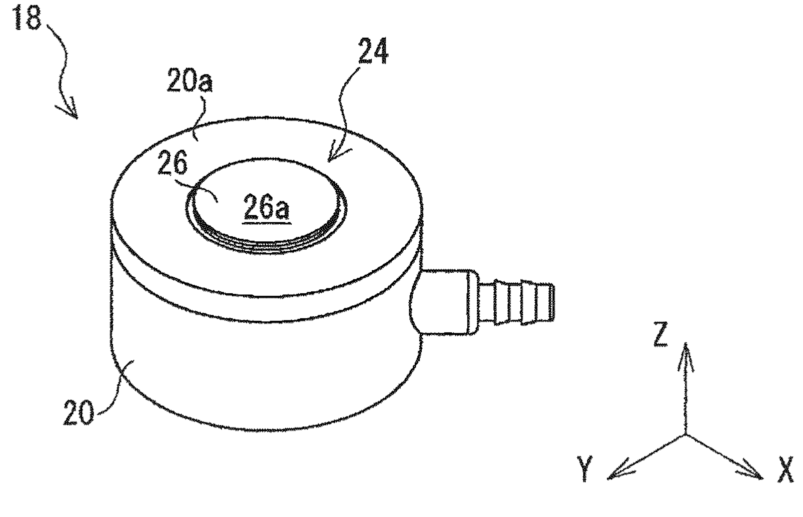
FIG. 2 is a perspective view of a chest piece.
Figure 3:
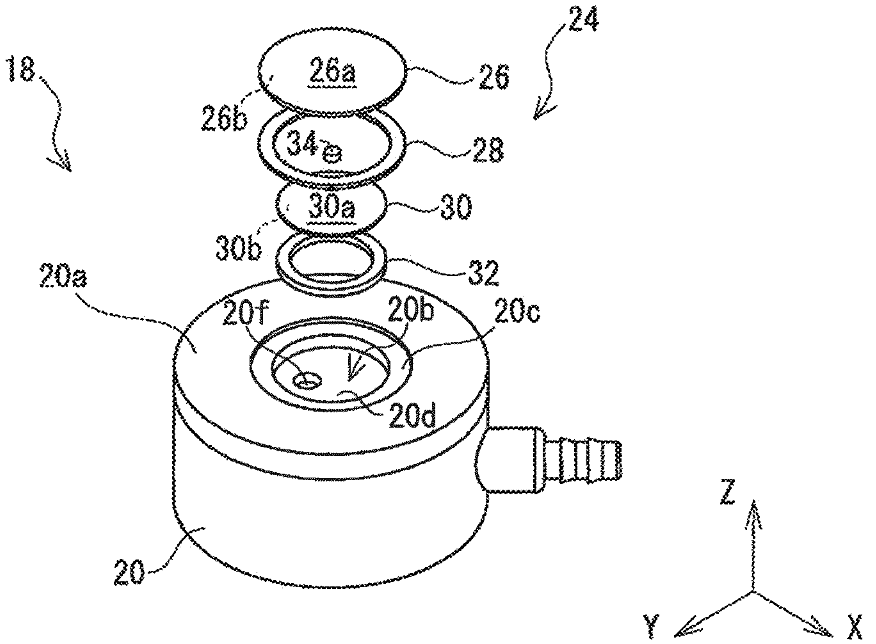
FIG. 3 is an exploded perspective view of the chest piece.
Figure 4:
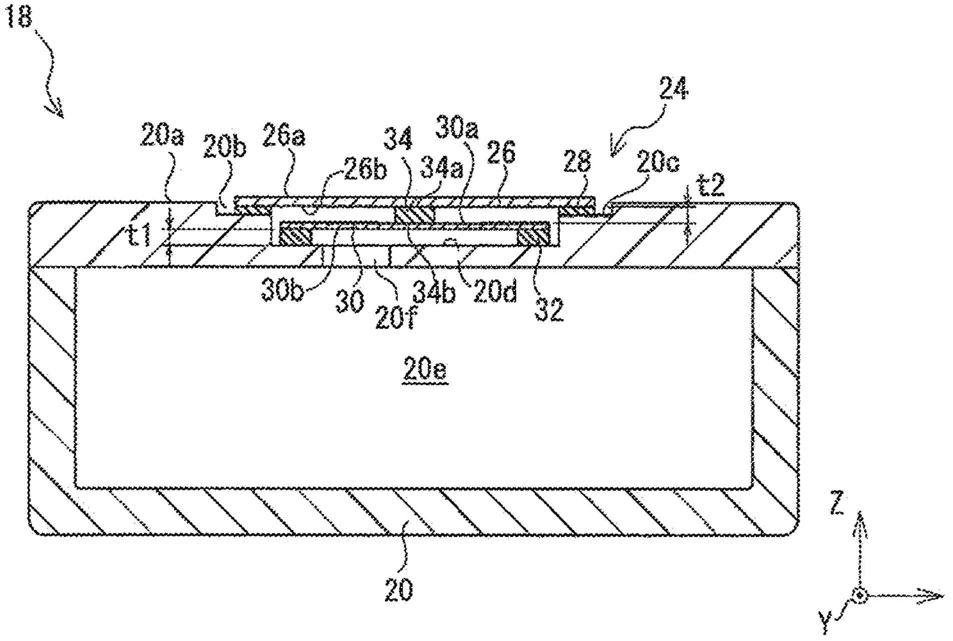
FIG. 4 is a sectional view of the chest piece.

FIG. 2 is a perspective view of the chest piece. Further, FIG. 3 is an exploded perspective view of the chest piece. Furthermore, FIG. 4 is a sectional view of the chest piece. Note that, an X-Y-Z orthogonal coordinate system in the figure is for facilitating the understanding of preferred embodiments of the present invention, and does not limit the present invention.

As illustrated in FIG. 2 and FIG. 3, the chest piece 18 includes a housing 20 of a columnar shape, for example. The housing 20 includes a contact surface 20*a* that comes into contact with a living body (a human, for example). In the case of Preferred Embodiment 1, as illustrated in FIG. 1, the contact surface 20*a* is covered with a cover 22 made of such as a silicon material. In the case above, the contact surface 20*a* comes into contact with a living body via the cover 22. Alternatively, the contact surface 20*a* may be in direct contact with the living body. Note that, in FIG. 2 and FIG. 3, the cover 22 is not illustrated.

In the case of Preferred Embodiment 1, a bioacoustic sensor 24 is fabricated by incorporating a plurality of elements into the housing 20.

Specifically, as illustrated in FIG. 3 and FIG. 4, the bioacoustic sensor 24 includes the housing 20 (the portion thereof), a diaphragm 26, a diaphragm support 28, a piezoelectric plate 30, a piezoelectric plate support 32, and a vibration transmitter 34.

In the case of Preferred Embodiment 1, the bioacoustic sensor 24 is configured by incorporating the plurality of elements into a recessed portion 20*b* on the contact surface 20*a* of the housing 20 in a stacked state.

The diaphragm 26 of the bioacoustic sensor 24 has a contact surface 26*a* in contact with a living body and a back surface 26*b* on the opposite side to the contact surface 26*a*. In the case of Preferred Embodiment 1, the contact surface 26*a* comes into contact with a living body via the cover 22. Further, the diaphragm 26 is a disk-shaped member made of a material that is not substantially compressively deformed, and is made of a metal material or hard resin, for example.

The diaphragm support 28 is provided to the housing 20 and supports the diaphragm 26, such that the diaphragm 26 is able to displace in the thickness direction (Z-axis direction) thereof. In the case of Preferred Embodiment 1, the diaphragm support 28 is made of a material that may elastically be deformed in the thickness direction, and is made of a sponge material, for example. Further, the diaphragm support 28 is an annular member extending along an outer peripheral edge of the diaphragm 26, and supports an outer side portion of the diaphragm 26 in the back surface 26*b*. The diaphragm support 28 is seated on a stepped portion 20*c* formed in the recessed portion 20*b* of the housing 20. The elastic deformation of such diaphragm support 28 in the thickness direction makes the diaphragm 26 be displaced in the thickness direction. That is, the diaphragm 26 may vibrate, for example. Thus, the diaphragm 26 may vibrate in synchronization with the vibration of a living body being in direct contact with via the contact surface 26*a*, or the vibration of a living body being in indirect contact with via the cover 22.

The piezoelectric plate 30 is a plate-shaped electronic component that converts vibration of the diaphragm 26 into a corresponding electric signal. Specifically, the piezoelectric plate 30 is deformed by vibration and generates an electric signal corresponding to the deformation amount. In the case of Preferred Embodiment 1, the piezoelectric plate 30 has a disc-shape. Further, the piezoelectric plate 30 includes a first surface 30*a* facing the back surface 26*b* of the diaphragm 26 with a gap therebetween, and a second surface 30*b* on the opposite side to the first surface 30*a*.

Figure 5:
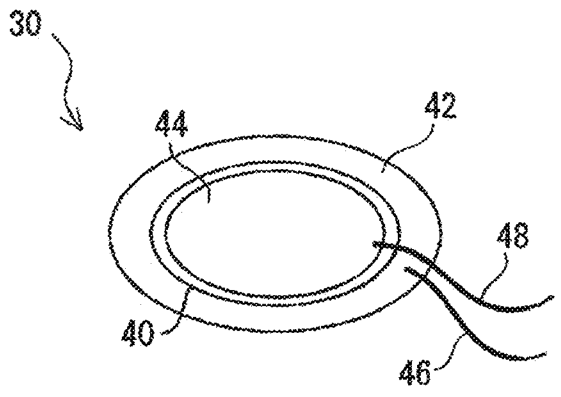
FIG. 5 is a perspective view of an example piezoelectric plate illustrating the details thereof.

FIG. 5 is a perspective view of an example piezoelectric plate illustrating the details thereof.

As illustrated in FIG. 5, the piezoelectric plate 30 is provided with a piezoelectric element 40, and a first electrode 42 and a second electrode 44 that sandwich and hold the piezoelectric element 40, for example. Further, the piezoelectric plate 30 is provided with a first signal line 46 electrically connected to the first electrode 42 and a second signal line 48 electrically connected to the second electrode 44. The deformation of the piezoelectric plate 30, that is, the deformation of the piezoelectric element 40 causes an electric potential difference between the first electrode 42 and the second electrode 44 to change. An electric signal (current) corresponding to the electric potential difference is outputted to the outside via the first signal line 46 and the second signal line 48.

Returning to FIG. 3 and FIG. 4, the piezoelectric plate support 32 is provided to the housing 20 and supports the second surface 30*b* of the piezoelectric plate 30. In the case of Preferred Embodiment 1, the piezoelectric plate support 32 is an annular body along the outer peripheral edge of the piezoelectric plate 30 and supports the outer side portion of the piezoelectric plate 30 in the second surface 30*b*. The piezoelectric plate support 32 is seated on a bottom surface 20*d* of the recessed portion 20*b* of the housing 20. Further, in the case of Preferred Embodiment 1, the piezoelectric plate support 32 is made of a material that may elastically be deformed in the thickness direction (Z-axis direction), and is made of sponge, for example. Thus, the piezoelectric plate support 32 has a hardness lower than that of the piezoelectric plate 30. Note that, in the present description, "hardness" represents the difficulty of deformation, and high "hardness" means that deformation is more difficult compared with low "hardness". Further, the piezoelectric plate support 32 is bonded to the second surface 30*b* of the piezoelectric plate 30 using an adhesive.

The vibration transmitter 34 is a member for transmitting the vibration of the diaphragm 26 to the piezoelectric plate 30 separated from the diaphragm 26. For the transmission, as illustrated in FIG. 4, the vibration transmitter 34 is sandwiched between the back surface 26*b* of the diaphragm 26 and the first surface 30*a* of the piezoelectric plate 30.

In the case of Preferred Embodiment 1, the vibration transmitter 34 includes a columnar body as illustrated in FIG. 3, and has a hardness (Shore hardness, Asker hardness, or Young's modulus, for example) higher than that of the piezoelectric plate support 32. The vibration transmitter 34 is made of a material having hardness higher than that of the material of the piezoelectric plate support 32, and is made of a metal or hard resin, for example. As an example, in the vibration transmitter 34 and the piezoelectric plate support 32, the former has a Shore hardness of approximately 30, and the latter has a Shore hardness of approximately 10.

Figure 6:
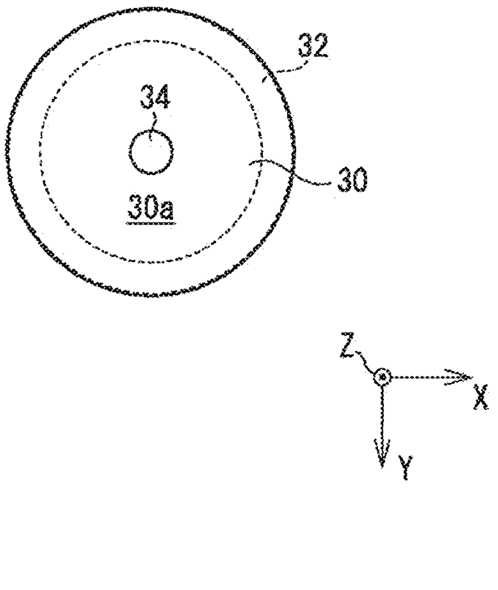
FIG. 6 is a top view of the bioacoustic sensor according to Preferred Embodiment 1 of the present invention illustrating a positional relationship between a piezoelectric plate support and a vibration transmitter.

FIG. 6 is a top view illustrating the positional relationship between the piezoelectric plate support and the vibration transmitter.

As illustrated in FIG. 6, the vibration transmitter 34 is positioned substantially on the center side portion of the piezoelectric plate 30 when viewed in the thickness direction (Z-axis direction). That is, the vibration transmitter 34 is positioned at a position closer to the center than the outer peripheral edge of the piezoelectric plate 30. Therefore, the vibration transmitter 34 is sandwiched and held between the center side portion of the diaphragm 26 and the center side portion of the piezoelectric plate 30.

Further, as illustrated in FIG. 6, in the case of Preferred Embodiment 1, the vibration transmitter 34 being a columnar body is surrounded by the piezoelectric plate support 32 being an annular body when viewed in the thickness direction (Z-axis direction). The reason for adopting such layout will be described later.

Further, in the case of Preferred Embodiment 1, as illustrated in FIG. 4, one end 34*a* of the vibration transmitter 34 is fixed to the back surface 26*b* of the diaphragm 26. For example, the vibration transmitter 34 is fixed to the diaphragm 26 using an adhesive. Similarly, another end 34*b* of the vibration transmitter 34 is fixed to the first surface 30*a* of the piezoelectric plate 30 using an adhesive. With this, the piezoelectric plate 30 may vibrate with substantially the same amplitude and frequency as the amplitude and frequency of the vibration of the diaphragm 26.

Up to here, the structure of the chest piece 18 of the stethoscope 10, that is, the structure of the bioacoustic sensor 24 has been described. Hereinafter, a control system of the stethoscope 10 will be described.

Figure 7:
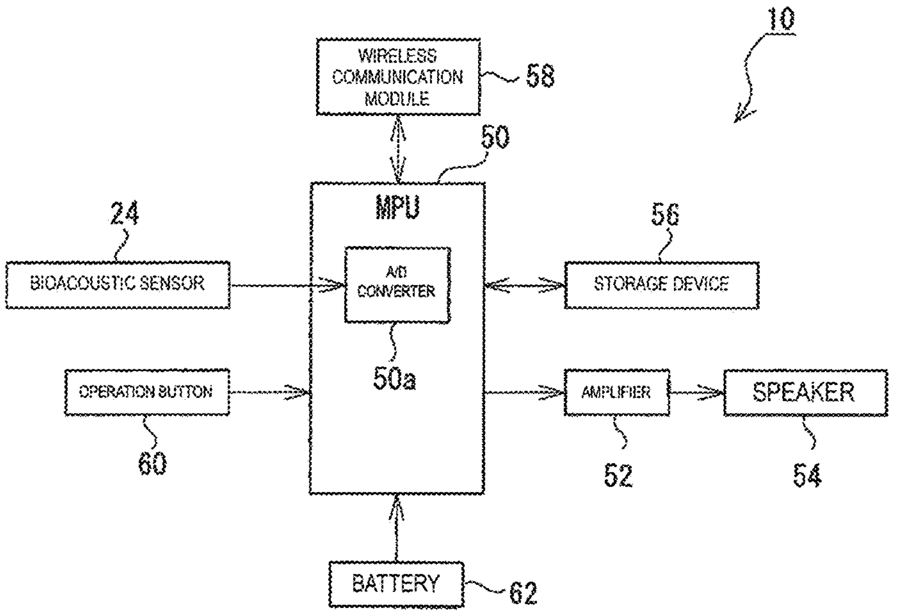
FIG. 7 is a block diagram of a control system of a stethoscope.

FIG. 7 is a block diagram of a control system of the stethoscope.

As illustrated in FIG. 7, the stethoscope 10 includes a microprocessor unit (MPU) 50 in addition to the bioacoustic sensor 24. The MPU 50 processes an electric signal from the bioacoustic sensor 24 (that is, piezoelectric plate 30). The MPU 50 includes an A/D converter 50*a* that converts an electric signal from analog to digital.

The electric signal from the bioacoustic sensor 24 that has been digitally processed by the MPU 50 is converted to a sound by an amplifier 52 and a speaker 54, and the sound is outputted through the Y-shaped tube 16, the ear tube 14, and the ear chip 12. When the chest piece 18 of the stethoscope 10 (that is, the contact surface 26*a* of the diaphragm 26) is in contact with the skin near the heart of a living body, a heart sound is outputted.

Further, the electric signal from the bioacoustic sensor 24 that has been digitally processed by the MPU 50 is stored as data in a storage device 56. For example, the storage device 56 is a memory card that is attachable to and detachable from the chest piece 18 of the stethoscope 10. When the chest piece 18 of the stethoscope 10 (that is, the contact surface 26*a* of the diaphragm 26) is in contact with the skin near the heart of a living body, heart sound data is stored.

Furthermore, the MPU 50 is configured or programmed to be able to transmit a digitally processed electric signal received from the bioacoustic sensor 24 to an external device (a computer, for example) in real time through a wireless communication module 58. The MPU 50 is also configured to transmit data such as the heart sound data stored in the storage device 56 to an external device through the wireless communication module 58. Note that, the wireless communication module 58 is a wireless communication module conforming to a digital wireless communication standard such as Bluetooth (registered trademark), for example.

In order to operate such MPU 50, a plurality of operation buttons 60 is provided on the housing 20 of the chest piece 18. By operating the operation button 60, the stethoscope 10 is started or stopped, for example. Further, by operating the operation button 60, modes are selected. The modes include a mode in which a digitally processed electric signal received from the bioacoustic sensor 24 is transmitted through the wireless communication module 58, a mode in which an electric signal is converted into a sound and the sound is outputted through the ear chip 12, and the like.

Further, a battery 62 to power and drive the MPU 50 is mounted on the chest piece 18. Note that the MPU 50, the amplifier 52, the speaker 54, the storage device 56, the wireless communication module 58, and the battery 62 are housed in an internal space 20*e* of the housing 20 illustrated in FIG. 4. In order to connect the MPU 50 housed in the internal space 20*e*, and the first signal line 46 and the second signal line 48 of the piezoelectric plate 30, an access hole 20*f* is provided in the housing 20. The access hole 20*f* makes the internal space 20*e* communicate with the recessed portion 20*b* of the housing 20 into which the piezoelectric plate 30 is incorporated.

Hereinafter, the operation of the bioacoustic sensor 24 will be described. Here, for the purpose of the description, an example will be described in which the contact surface 20*a* of the housing 20 of the chest piece 18 is in contact with the skin near a heart in order to auscultate the heart sound of a living body (a human, for example) using the stethoscope 10.

The pulsation of a heart makes the diaphragm 26 of the bioacoustic sensor 24 be repeatedly displaced, that is, the diaphragm 26 of the bioacoustic sensor 24 vibrates.

Figure 8:
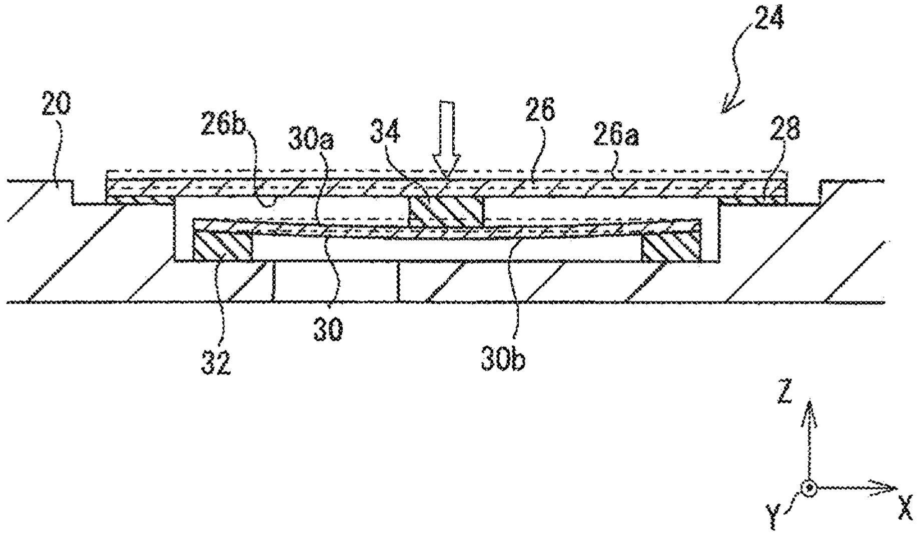
FIG. 8 is a sectional view of the bioacoustic sensor according to Preferred Embodiment 1 of the present invention illustrating a state in which the piezoelectric plate is deformed.

FIG. 8 is a sectional view of the bioacoustic sensor according to Preferred Embodiment 1 illustrating a state in which the piezoelectric plate is deformed. In FIG. 8, an alternate long and two short dashes line indicates a state in which the piezoelectric plate is not deformed, that is, a state in which no force is applied to the diaphragm.

Specifically, as illustrated in FIG. 8, the diaphragm 26 reciprocates in the thickness direction (Z-axis direction) without being substantially deformed by the pulsation of a heart. With this, the center side portion of the piezoelectric plate 30, connected to the diaphragm 26 via the vibration transmitter 34 being a columnar body, reciprocates in the thickness direction in the same manner as the diaphragm 26.

As a result, the piezoelectric plate 30 repeats flexural deformation in which the center side portion thereof is displaced in the thickness direction (Z-axis direction) relative to the outer side portion. This is because the outer side portion of the second surface 30*b* of the piezoelectric plate 30 is supported by the piezoelectric plate support 32 being an annular body, in other words, there is no member to support the center side portion of the second surface 30*b*.

That is, in the piezoelectric plate 30, the center side portion of the first surface 30*a* thereof is restrained by the vibration transmitter 34, and the outer side portion of the second surface 30*b* thereof is restrained by the piezoelectric plate support 32. Because of the above, the piezoelectric plate 30 is connected to the diaphragm 26 via the vibration transmitter 34 in a state in which the center side portion is easily displaced (easily flexurally deformed) in the thickness direction (Z-axis direction) relative to the outer side portion.

Since the vibration of the diaphragm 26 causes the piezoelectric plate 30 to repeat the flexural deformation, the piezoelectric plate 30 may detect the vibration of the diaphragm 26 with high sensitivity. That is, the piezoelectric plate 30 may detect the vibration of the diaphragm 26 with higher sensitivity than in a case that the entire first surface 30*a* of the piezoelectric plate 30 is attached to the back surface 26*b* of the diaphragm 26. For example, even when the amplitude of the vibration of the diaphragm 26 is small or the frequency is high, the piezoelectric plate 30 may detect the vibration of the diaphragm 26.

In order to make the flexural deformation of the piezoelectric plate 30 easy, as illustrated in FIG. 6, it is preferable that a distance between the piezoelectric plate support 32 and the vibration transmitter 34 be large when viewed in the thickness direction (Z-axis direction). However, it is preferable that a contact area between the vibration transmitter 34 and the first surface 30*a* of the piezoelectric plate 30 be large in consideration of transmission efficiency of the vibration from the diaphragm 26 to the piezoelectric plate 30. In consideration of the above issues, it is preferable that a radius of the vibration transmitter 34 be smaller than about 50% of a radius of the piezoelectric plate 30, for example.

Further, as described above, in the case of Preferred Embodiment 1, the piezoelectric plate support 32 has a hardness lower than that of the vibration transmitter 34 and the piezoelectric plate 30. With this, it is possible to prevent the piezoelectric plate 30 from being flexurally deformed with an excessively large deformation amount to be damaged. That is, even when the center side portion of the piezoelectric plate 30 is pressed by the vibration transmitter 34 to be excessively displaced, the outer side portion of the piezoelectric plate 30 may be displaced while compressing the piezoelectric plate support 32. As a result, the excessive flexural deformation of the piezoelectric plate 30 is reduced or prevented.

Note that, the excessive flexural deformation of the piezoelectric plate 30 may be reduced or prevented by limiting a stroke range of the diaphragm 26 in the thickness direction (Z-axis direction). For example, by manufacturing the diaphragm support 28 with a material having an appropriate elastic modulus or by providing a stopper, it is possible to reduce or prevent the displacement of the diaphragm 26 with an excessive displacement amount, that is, to reduce or prevent the excessive flexural deformation of the piezoelectric plate 30. In the case above, the piezoelectric plate support 32 and the vibration transmitter 34 may have the same hardness.

In order to be able to reduce or prevent the excessive flexural deformation of the piezoelectric plate 30, as illustrated in FIG. 4, a thickness (size in the Z-axis direction) t1 of the piezoelectric plate support 32 may be determined. Specifically, the thickness t1 of the piezoelectric plate support 32 is determined as follows. When a predetermined force or more is applied to the diaphragm 26 and the piezoelectric plate 30 is flexurally deformed, the center of the second surface 30*b* of the piezoelectric plate 30 is brought into contact with the bottom surface 20*d* of the recessed portion 20*b* of the housing 20. The "predetermined force" referred to herein is the force that is smaller than the force with which the piezoelectric plate 30 is damaged, and larger than the maximum force that may be applied to the diaphragm 26 in normal use of the bioacoustic sensor 24. With this, the excessive flexural deformation of the piezoelectric plate 30 is reduced or prevented, and damage to the piezoelectric plate 30 is reduced or prevented.

Instead of the thickness t1 of the piezoelectric plate support 32, a thickness (size in the Z-axis direction) t2 of the vibration transmitter 34 may appropriately be determined to reduce or prevent the excessive flexural deformation of the piezoelectric plate 30. Specifically, the thickness t2 of the vibration transmitter 34 is determined as follows. When a predetermined force or more is applied to the diaphragm 26 and the piezoelectric plate 30 is flexurally deformed, the outer peripheral edge of the first surface 30*a* of the piezoelectric plate 30 is brought into contact with the diaphragm 26.

Furthermore, as described above, since the piezoelectric plate support 32 is made of an elastically deformable material, the piezoelectric plate support 32 is able to function as a damper that absorbs vibration. For example, the piezoelectric plate support 32 is able to absorb undesirable high frequency components derived from a rubbing sound generated between a living body and the contact surface 26*a* of the diaphragm 26.

According to Preferred Embodiment 1 described above, in the bioacoustic sensor 24 including the piezoelectric plate 30, the vibration detection sensitivity may be increased.

Preferred Embodiment 2

Preferred Embodiment 2 is substantially the same as Preferred Embodiment 1 described above except for the shapes of the piezoelectric plate support and the vibration transmitter. Therefore, Preferred Embodiment 2 will be described focusing on the differences. Note that, substantially the same elements as those of Preferred Embodiment 1 described above are denoted by the same reference signs.

Figure 9:
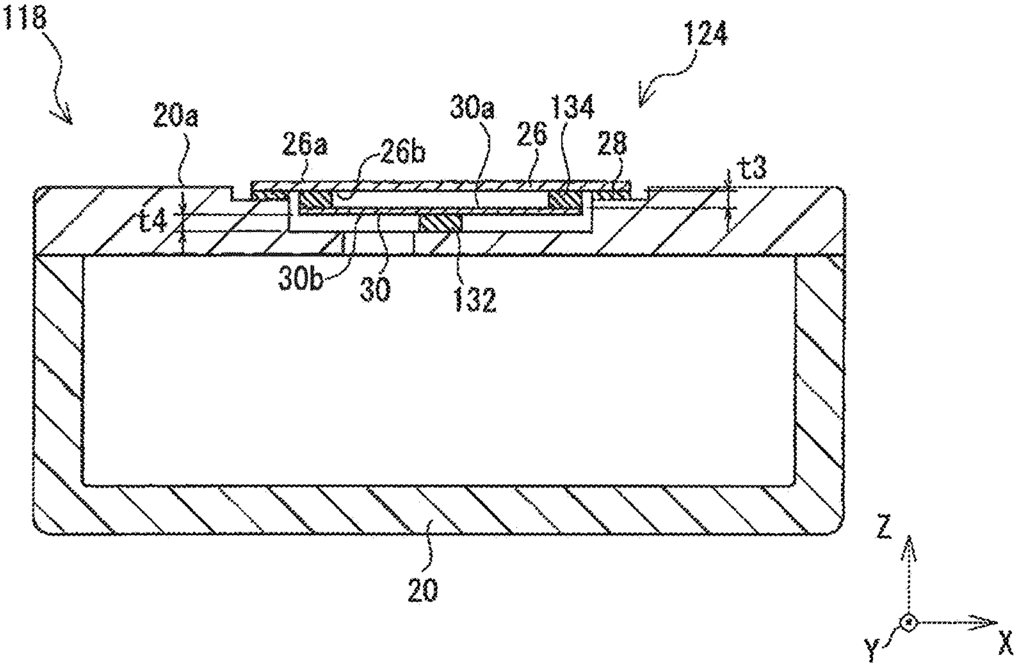
FIG. 9 is a sectional view of a chest piece in a stethoscope including a bioacoustic sensor according to Preferred Embodiment 2 of the present invention.
Figure 10:
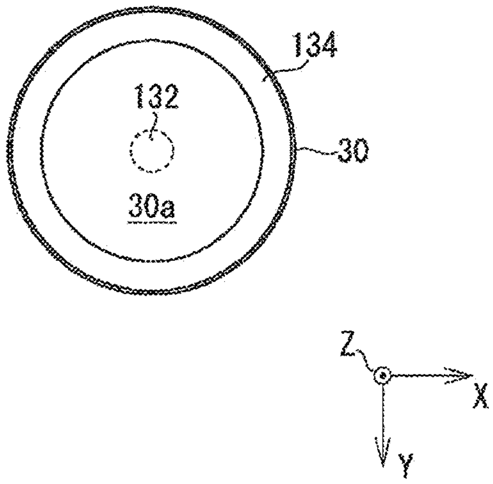
FIG. 10 is a top view of the bioacoustic sensor according to Preferred Embodiment 2 of the present invention illustrating a positional relationship between a piezoelectric plate support and a vibration transmitter.

FIG. 9 is a sectional view of a chest piece in a stethoscope including a bioacoustic sensor according to Preferred Embodiment 2. Further, FIG. 10 is a top view illustrating the positional relationship between the piezoelectric plate support and the vibration transmitter.

As illustrated in FIG. 9, in a bioacoustic sensor 124 provided to a chest piece 118 of the stethoscope according to Preferred Embodiment 2, a piezoelectric plate support 132 is a columnar body positioned substantially on the center side portion of the piezoelectric plate 30 when viewed in the thickness direction (Z-axis direction). Whereas, a vibration transmitter 134 is an annular body along the outer peripheral edge of the piezoelectric plate 30. Therefore, as illustrated in FIG. 10, the vibration transmitter 134 being an annular body surrounds the piezoelectric plate support 132 being a columnar body when viewed in the thickness direction.

Figure 11:
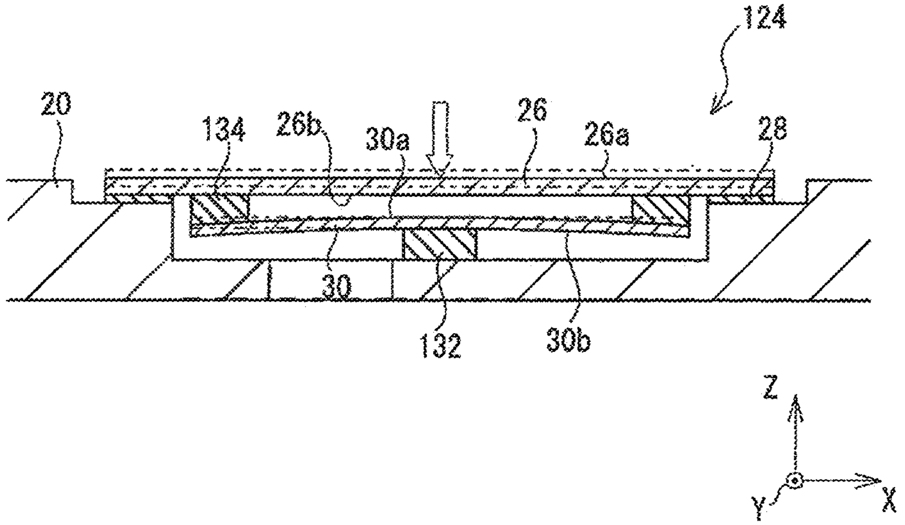
FIG. 11 is a sectional view of the bioacoustic sensor according to Preferred Embodiment 2 of the present invention illustrating a state in which a piezoelectric plate is deformed.

FIG. 11 is a sectional view of the bioacoustic sensor according to Preferred Embodiment 2 illustrating a state in which the piezoelectric plate is deformed. In FIG. 11, an alternate long and two short dashes line indicates a state in which the piezoelectric plate is not deformed, that is, a state in which no force is applied on the diaphragm.

As illustrated in FIG. 11, the diaphragm 26 reciprocates in the thickness direction (Z-axis direction) because of the vibration (pulsation of a heart, for example) of a living body in contact with the diaphragm 26. With this, the outer side portion of the piezoelectric plate 30, connected to the diaphragm 26 via the vibration transmitter 134 being an annular body, reciprocates in the thickness direction in the same manner as the diaphragm 26.

Meanwhile, since the center side portion of the second surface 30*b* of the piezoelectric plate 30 is supported by the piezoelectric plate support 132 being a columnar body, the piezoelectric plate 30 repeats flexural deformation in which the outer side portion thereof is displaced in the thickness direction (Z-axis direction) relative to the center side portion.

That is, in the case of Preferred Embodiment 1 described above, as illustrated in FIG. 8, the piezoelectric plate 30 is flexurally deformed in a concave shape, but in the case of Preferred Embodiment 2, as illustrated in FIG. 11, the piezoelectric plate 30 is flexurally deformed in a convex shape.

Note that, in order to be able to reduce or prevent the excessive flexural deformation of the piezoelectric plate 30, as illustrated in FIG. 9, a thickness (size in the Z-axis direction) t3 of the vibration transmitter 134 may be determined. Specifically, the thickness t3 of the vibration transmitter 134 is determined as follows. When a predetermined force or more is applied to the diaphragm 26 and the piezoelectric plate 30 is flexurally deformed, the center of the first surface 30*a* of the piezoelectric plate 30 is brought into contact with the diaphragm 26. The "predetermined force" referred to herein is the force that is smaller than the force with which the piezoelectric plate 30 is damaged, and larger than the maximum force that may be applied to the diaphragm 26 in normal use of the bioacoustic sensor 124. With this, the excessive flexural deformation of the piezoelectric plate 30 is reduced or prevented, and damage to the piezoelectric plate 30 is reduced or prevented.

Instead of the thickness t3 of the vibration transmitter 134, a thickness (size in the Z-axis direction) t4 of the piezoelectric plate support 132 may appropriately be determined to reduce or prevent the excessive flexural deformation of the piezoelectric plate 30. Specifically, the thickness t4 of the piezoelectric plate support 132 is determined as follows. When a predetermined force or more is applied to the diaphragm 26 and the piezoelectric plate 30 is flexurally deformed, the outer peripheral edge of the second surface

30*b* of the piezoelectric plate 30 is brought into contact with the bottom surface 20*d* of the recessed portion 20*b* of the housing 20.

Also in such Preferred Embodiment 2, similar to Preferred Embodiment 1 described above, the vibration detection sensitivity may be increased in the bioacoustic sensor 124 including the piezoelectric plate 30.

Preferred Embodiment 3

Preferred Embodiment 3 is substantially the same as Preferred Embodiment 1 described above except for the vibration transmitter. Therefore, Preferred Embodiment 3 will be described focusing on the differences. Note that, substantially the same elements as those of Preferred Embodiment 1 described above are denoted by the same reference signs.

Figure 12:
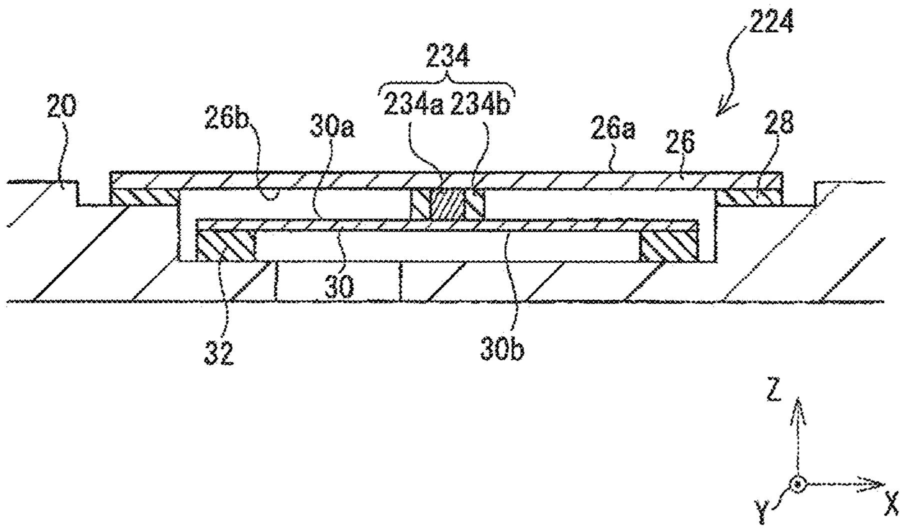
FIG. 12 is a sectional view of a portion of a chest piece of a stethoscope including a bioacoustic sensor according to Preferred Embodiment 3 of the present invention.

FIG. 12 is a sectional view of a portion of a chest piece of a stethoscope including a bioacoustic sensor according to Preferred Embodiment 3.

As illustrated in FIG. 12, in a bioacoustic sensor 224 according to Preferred Embodiment 3, a vibration transmitter 234 is a columnar body, and is a member having a lower hardness in the outer side portion than in the center side portion. For example, the vibration transmitter 234 is manufactured by forming an elastic layer 234*b* on an outer peripheral surface of a metal core body 234*a*.

Such vibration transmitter 234 alleviates the stress concentration in the portion of the piezoelectric plate 30 which comes into contact with the corner of the end surface of the vibration transmitter 234. As a result, damage to the piezoelectric plate 30 due to the stress concentration may be reduced or prevented.

Also in such Preferred Embodiment 3, similar to Preferred Embodiment 1 described above, the vibration detection sensitivity may be increased in the bioacoustic sensor 224 including the piezoelectric plate 30.

Note that, such structure of the vibration transmitter 234 having a lower hardness in the outer side portion than in the center side portion may also be used in the piezoelectric plate support 132 of the bioacoustic sensor 124 according to Preferred Embodiment 2 described above.

Preferred Embodiment 4

Preferred Embodiment 4 is substantially the same as Preferred Embodiment 1 described above except for the vibration transmitter. Therefore, Preferred Embodiment 4 will be described focusing on the differences. Note that, substantially the same elements as those of Preferred Embodiment 1 described above are denoted by the same reference signs.

Figure 13:
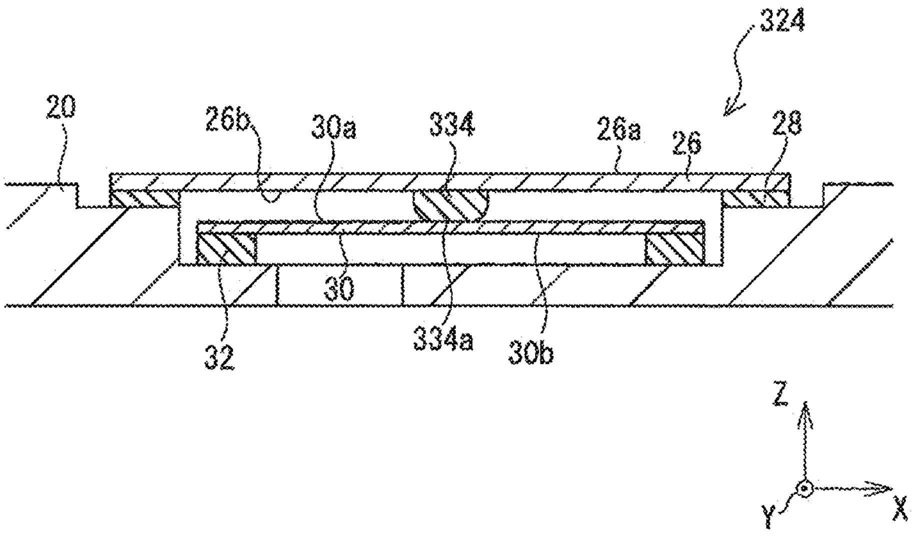
FIG. 13 is a sectional view of a portion of a chest piece of a stethoscope including a bioacoustic sensor according to Preferred Embodiment 4 of the present invention.

FIG. 13 is a sectional view of a portion of a chest piece of a stethoscope including a bioacoustic sensor according to Preferred Embodiment 4.

As illustrated in FIG. 13, in a bioacoustic sensor 324 according to Preferred Embodiment 4, a vibration transmitter 334 is a columnar body. An end surface 334*a* of the vibration transmitter 334 in contact with the piezoelectric plate 30 includes a rounded corner. That is, the end surface 334*a* of the vibration transmitter 334 does not have a sharp corner (a corner having an angle of 90°, for example) being in contact with the piezoelectric plate 30 that causes stress concentration in the contact portion. As a result, damage to the piezoelectric plate 30 due to the stress concentration may be reduced or prevented.

Also in such Preferred Embodiment 4, similar to Preferred Embodiment 1 described above, the vibration detection sensitivity may be increased in the bioacoustic sensor 324 including the piezoelectric plate 30.

Note that, such rounded corner structure of the end surface 334*a* of the vibration transmitter 334 may also be used in the piezoelectric plate support 132 of the bioacoustic sensor 124 according to Preferred Embodiment 2 described above.

Preferred Embodiment 5

In the case of Preferred Embodiment 1 described above, as illustrated in FIG. 4, the vibration transmitter 34 and an air layer are present between the diaphragm 26 and the piezoelectric plate 30. Further, the piezoelectric plate support 32 and an air layer are present between the piezoelectric plate 30 and the housing 20. Preferred Embodiment 5 does not have such an air layer. Therefore, Preferred Embodiment 5 will be described focusing on the differences. Note that, substantially the same elements as those of Preferred Embodiment 1 described above are denoted by the same reference signs.

Figure 14:
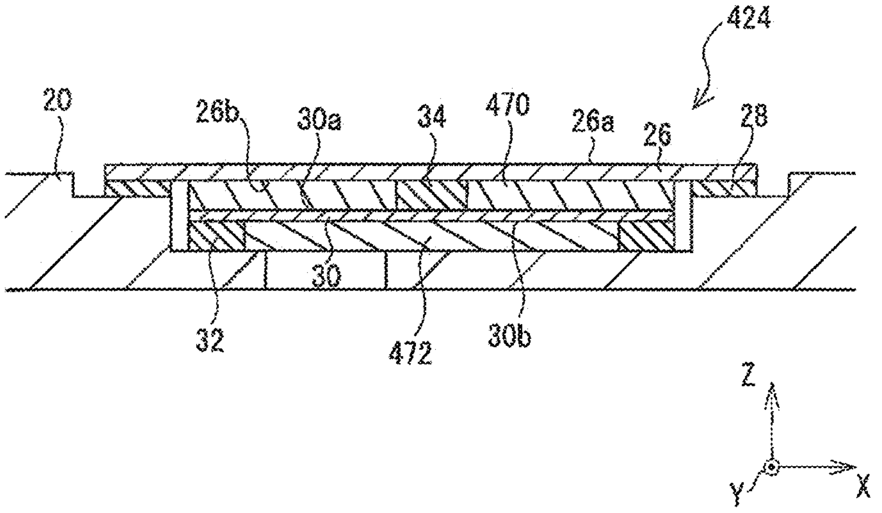
FIG. 14 is a sectional view of a portion of a chest piece of a stethoscope including a bioacoustic sensor according to Preferred Embodiment 5 of the present invention.

FIG. 14 is a sectional view of a portion of a chest piece of a stethoscope including a bioacoustic sensor according to Preferred Embodiment 5.

As illustrated in FIG. 14, a bioacoustic sensor 424 according to Preferred Embodiment 5 includes a first damper 470 disposed between the diaphragm 26 and the piezoelectric plate 30, and a second damper 472 disposed between the piezoelectric plate 30 and the housing 20.

The first damper 470 has a hardness lower than that of the vibration transmitter 34 disposed between the diaphragm 26 and the piezoelectric plate 30 similar to the first damper 470. For example, when the vibration transmitter 34 is made of a metal material, the first damper 470 is made of a sponge material.

The second damper 472 has a hardness lower than that of the piezoelectric plate support 32 disposed between the piezoelectric plate 30 and the housing 20 similar to the second damper 472. For example, the piezoelectric plate support 32 is made of a material having a relatively high elastic modulus, and the second damper 472 is made of a material having a relatively low elastic modulus.

With the use of such first damper 470 and second damper 472, it is possible to reduce or prevent the contact between the diaphragm 26 and the piezoelectric plate 30, and the contact between the piezoelectric plate 30 and the housing 20. Further, it is possible to reduce or prevent the flexural deformation due to the own weights of the diaphragm 26 and the piezoelectric plate 30, that is, it is possible to reduce or prevent continuous flexural deformation during non-use.

Also in Preferred Embodiment 5, similar to Preferred Embodiment 1 described above, the vibration detection sensitivity may be increased in the bioacoustic sensor 424 including the piezoelectric plate 30.

Note that, such first damper 470 and second damper 472 may also be included in the bioacoustic sensor 124 according to Preferred Embodiment 2 described above.

Preferred Embodiment 6

In the case of Preferred Embodiment 1 described above, as illustrated in FIG. 4, the housing 20 indirectly supports the outer side portion of the second surface 30*b* of the piezoelectric plate 30 via the piezoelectric plate support 32 being an annular body. Unlike the above, in the case of Preferred Embodiment 6, the housing directly supports the piezoelectric plate. Preferred Embodiment 6 will be described focusing on the differences. Note that, substantially the same elements as those of Preferred Embodiment 1 described above are denoted by the same reference signs.

Figure 15:
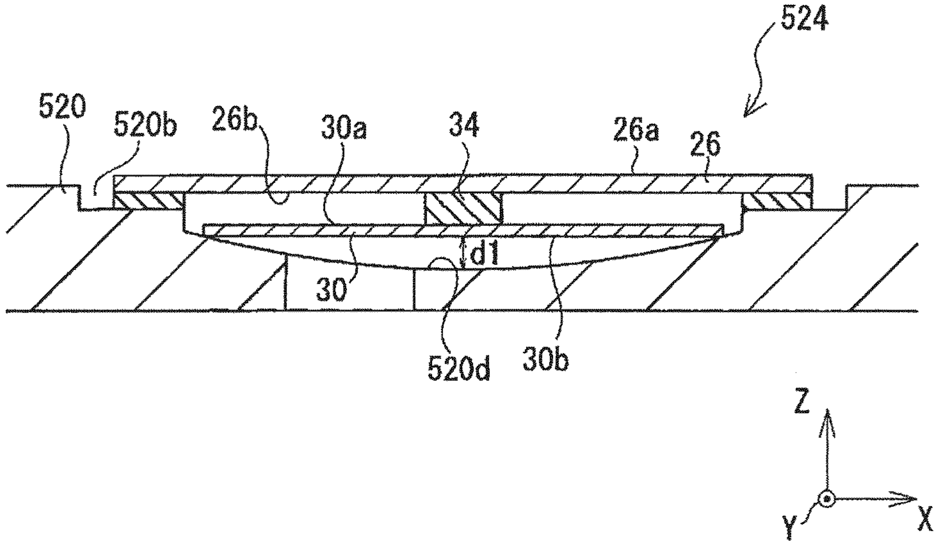
FIG. 15 is a sectional view of a portion of a chest piece of a stethoscope including a bioacoustic sensor according to Preferred Embodiment 6 of the present invention.

FIG. 15 is a sectional view of a portion of a chest piece of a stethoscope including a bioacoustic sensor according to Preferred Embodiment 6.

As illustrated in FIG. 15, in a bioacoustic sensor 524 according to Preferred Embodiment 6, the outer side portion of the second surface 30*b* of the piezoelectric plate 30 is directly supported by a bottom surface 520*d* of a recessed portion 520*b* of a housing 520. To achieve the above, the bottom surface 520*d* includes a concave surface. The concave-shaped bottom surface 520*d* is provided in the housing 520 such that the lowermost portion faces the center of the second surface 30*b* of the piezoelectric plate 30 in the thickness direction (Z-axis direction). Since the outer side portion of the second surface 30*b* is supported by the concave-shaped bottom surface 520*d*, the piezoelectric plate 30 may flexurally be deformed in accordance with the force applied to the diaphragm 26.

Note that, in order to be able to reduce or prevent the excessive flexural deformation of the piezoelectric plate 30, as illustrated in FIG. 15, there may be determined a distance d1 from the center of the second surface 30*b* of the piezoelectric plate 30 to the concave-shaped bottom surface 520*d* of the housing 520. For example, the distance d1 is about 50 μm. Specifically, the distance d1 is determined as follows. When a predetermined force or more is applied to the diaphragm 26 and the piezoelectric plate 30 is flexurally deformed, the center of the second surface 30*b* of the piezoelectric plate 30 comes into contact with the concave-shaped bottom surface 520*d*. The “predetermined force” referred to herein is the force that is smaller than the force with which the piezoelectric plate 30 is damaged, and larger than the maximum force that may be applied to the diaphragm 26 in normal use of the bioacoustic sensor 524. With this, the excessive flexural deformation of the piezoelectric plate 30 is reduced or prevented, and damage to the piezoelectric plate 30 is reduced or prevented.

When a predetermined force or more is applied to the diaphragm 26, the entire second surface 30*b* of the piezoelectric plate 30 comes into contact with the bottom surface 520*d* of the recessed portion 520*b* of the housing 520. With this, the compressive stress in the piezoelectric plate 30 in the vicinity portion of the second surface 30*b* is uniformly or substantially uniformly distributed, thus reducing or preventing local excessive deformation of the piezoelectric plate 30 such as buckling or cracking, for example. As a result, damage to the piezoelectric plate 30 is reduced or prevented.

Also in such Preferred Embodiment 6, similar to Preferred Embodiment 1 described above, the vibration detection sensitivity may be increased in the bioacoustic sensor 524 including the piezoelectric plate 30.

Preferred Embodiment 7

Preferred Embodiment 7 is an improved form of Preferred Embodiment 6 described above. Therefore, Preferred Embodiment 7 will be described focusing on the differences. Note that, substantially the same elements as those of Preferred Embodiment 6 described above are denoted by the same reference signs.

Figure 16:
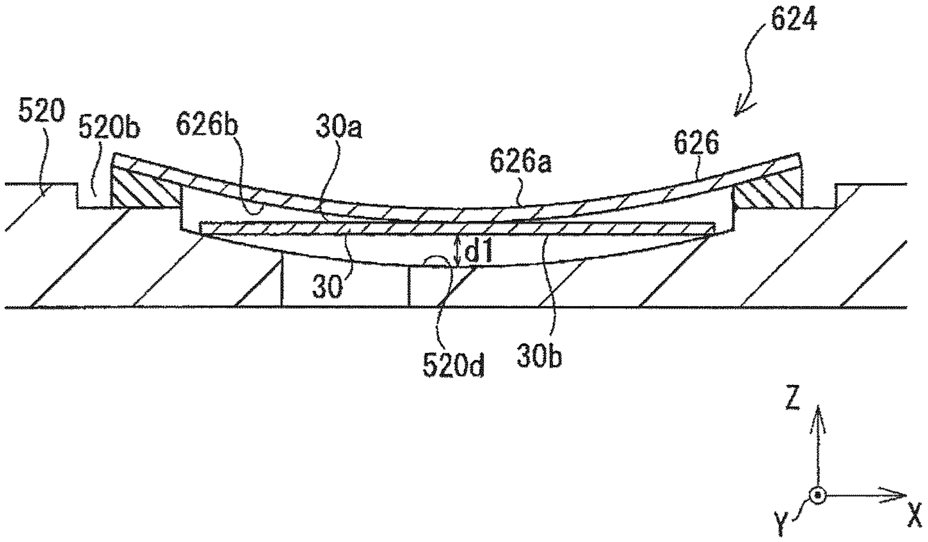
FIG. 16 is a sectional view of a portion of a chest piece of a stethoscope including a bioacoustic sensor according to Preferred Embodiment 7 of the present invention.

FIG. 16 is a sectional view of a portion of a chest piece of a stethoscope including a bioacoustic sensor according to Preferred Embodiment 7.

As illustrated in FIG. 16, in a bioacoustic sensor 624 according to Preferred Embodiment 7, the piezoelectric plate 30 is directly supported by the concave-shaped bottom surface 520*d* of the recessed portion 520*b* of the housing 520 in the outer side portion of the second surface 30*b*. Further, a diaphragm 626 is in direct contact with the center side portion of the first surface 30*a* of the piezoelectric plate 30 without a vibration transmitter interposed therebetween. To achieve the above, the diaphragm 626 is provided with a convex surface on a back surface 626*b* thereof. In the case of Preferred Embodiment 7, the diaphragm 626 has a shape in which the center side portion thereof is curved to be convex toward the side of the piezoelectric plate 30 in a natural state (a state in which no force is applied). The center (vertex) of the convex-shaped back surface 626*b* is in direct contact with the first surface 30*a* of the piezoelectric plate 30.

Further, the convex shape of the back surface 626*b* of the diaphragm 626 corresponds to the concave shape of the bottom surface 520*d* of the recessed portion 520*b* of the housing 520. That is, the back surface 626*b* and the bottom surface 520*d* are parallel to each other. Therefore, when a predetermined force or more is applied to the diaphragm 626, the entire second surface 30*b* of the piezoelectric plate 30 comes into contact with the bottom surface 520*d* of the recessed portion 520*b* of the housing 520, and also the entire first surface 30*a* of the piezoelectric plate 30 comes into contact with the back surface 626*b* of the diaphragm 626. That is, the entire piezoelectric plate 30 is sandwiched and held between the diaphragm 626 and the housing 520. With this, the compressive stress is uniformly or substantially uniformly distributed over the entire piezoelectric plate 30, thus reducing or preventing the local excessive deformation of the piezoelectric plate 30 such as buckling or cracking, for example. As a result, damage to the piezoelectric plate 30 is suppressed.

Also in such Preferred Embodiment 7, similar to Preferred Embodiment 1 described above, the vibration detection sensitivity may be increased in the bioacoustic sensor 624 including the piezoelectric plate 30.

Preferred Embodiment 8

In the case of Preferred Embodiment 2 described above, as illustrated in FIG. 9, the diaphragm 26 is in indirect contact with the outer side portion of the first surface 30*a* of the piezoelectric plate 30 via the vibration transmitter 134 being an annular body. Unlike the above, in the case of Preferred Embodiment 8, the diaphragm is in direct contact with the piezoelectric plate. Preferred Embodiment 8 will be described focusing on the differences. Note that, substantially the same elements as those of Preferred Embodiment 2 described above are denoted by the same reference signs.

Figure 17:
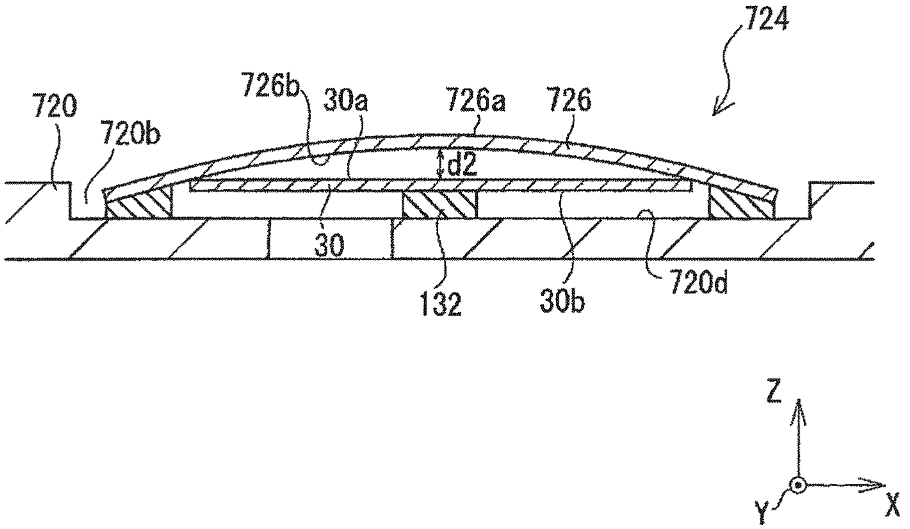
FIG. 17 is a sectional view of a portion of a chest piece of a stethoscope including a bioacoustic sensor according to Preferred Embodiment 8 of the present invention.

FIG. 17 is a sectional view of a portion of a chest piece of a stethoscope including a bioacoustic sensor according to Preferred Embodiment 8.

As illustrated in FIG. 17, in a bioacoustic sensor 724 according to Preferred Embodiment 8, a back surface 726*b* of a diaphragm 726 is in direct contact with the outer side portion of the first surface 30*a* of the piezoelectric plate 30. To achieve the above, the back surface 726*b* is configured with a concave surface. In the case of Preferred Embodiment 8, the diaphragm 726 has a shape in which the center side portion thereof is curved to be concave toward the side of the piezoelectric plate 30 in a natural state (a state in which no force is applied). The concave-shaped back surface 726*b* is formed on the diaphragm 726 such that the uppermost portion faces the center of the first surface 30*a* of the piezoelectric plate 30 in the thickness direction (Z-axis direction). Since the concave-shaped back surface 726*b* comes into contact with the outer side portion of the first surface 30*a*, the piezoelectric plate 30 may flexurally be deformed in accordance with the force applied to the diaphragm 726.

Note that, in order to be able to reduce or prevent the excessive flexural deformation of the piezoelectric plate 30, as illustrated in FIG. 17, there may be determined a distance d2 from the center of the first surface 30*a* of the piezoelectric plate 30 to the concave-shaped back surface 726*b* of the diaphragm 726. For example, the distance d2 is about 50 μm. Specifically, the distance d2 is determined as follows. When a predetermined force or more is applied to the diaphragm 726 and the piezoelectric plate 30 is flexurally deformed, the center of the first surface 30*a* of the piezoelectric plate 30 comes into contact with the concave-shaped back surface 726*b*. The "predetermined force" referred to herein is the force that is smaller than the force with which the piezoelectric plate 30 is damaged, and larger than the maximum force that may be applied to the diaphragm 726 in normal use of the bioacoustic sensor 724. With this, the excessive flexural deformation of the piezoelectric plate 30 is reduced or prevented, and damage to the piezoelectric plate 30 is reduced or prevented.

When a predetermined force or more is applied to the diaphragm 726, the entire first surface 30*a* of the piezoelectric plate 30 comes into contact with the back surface 726*b* of the diaphragm 726. With this, the compressive stress in the piezoelectric plate 30 in the vicinity portion of the first surface 30*a* is substantially uniformly distributed, thus reducing or preventing the local excessive deformation of the piezoelectric plate 30 such as buckling or cracking, for example. As a result, damage to the piezoelectric plate 30 is reduced or prevented.

Also in such Preferred Embodiment 8, similar to Preferred Embodiment 2 described above, the vibration detection sensitivity may be increased in the bioacoustic sensor 724 including the piezoelectric plate 30.

Preferred Embodiment 9

Preferred Embodiment 9 is an improved form of Embodiment 8 described above. Therefore, Preferred Embodiment 9 will be described focusing on the differences. Note that, substantially the same elements as those of Preferred Embodiment 8 described above are denoted by the same reference signs.

Figure 18:
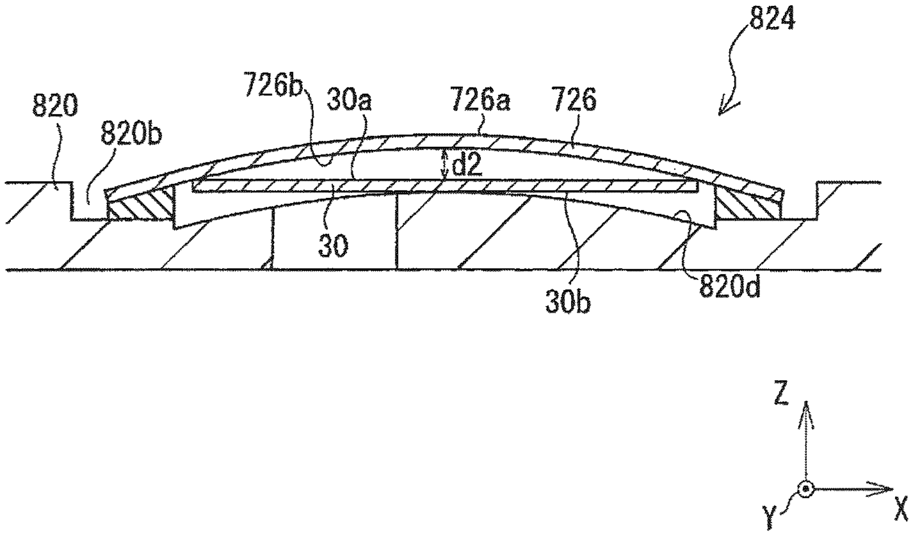
FIG. 18 is a sectional view of a portion of a chest piece of a stethoscope including a bioacoustic sensor according to Preferred Embodiment 9 of the present invention.

FIG. 18 is a sectional view of a portion of a chest piece of a stethoscope including a bioacoustic sensor according to Preferred Embodiment 9.

As illustrated in FIG. 18, in a bioacoustic sensor 824 according to Preferred Embodiment 9, the concave-shaped back surface 726*b* of the diaphragm 726 is in direct contact with the outer side portion of the first surface 30*a* of the piezoelectric plate 30. Further, a bottom surface 820*d* of a recessed portion 820*b* of a housing 820 is in direct contact with the center side portion of the second surface 30*b* of the piezoelectric plate 30 without a piezoelectric plate support interposed therebetween. To achieve the above, a convex surface is provided on the bottom surface 820*d* of the housing 820. The center (vertex) of the convex-shaped bottom surface 820*d* is in direct contact with the second surface 30*b* of the piezoelectric plate 30.

Further, the convex shape of the bottom surface 820*d* of the recessed portion 820*b* of the housing 820 corresponds to the concave shape of the back surface 726*b* of the diaphragm 726. That is, the bottom surface 820*d* and the back surface 726*b* are parallel to each other. Therefore, when a predetermined force or more is applied to the diaphragm 726, the entire first surface 30*a* of the piezoelectric plate 30 comes into contact with the back surface 726*b* of the diaphragm 726, and also the entire second surface 30*b* of the piezoelectric plate 30 comes into contact with the bottom surface 820*d* of the recessed portion 820*b* of the housing 820. That is, the entire piezoelectric plate 30 is sandwiched and held between the diaphragm 726 and the housing 820. With this, the compressive stress is uniformly or substantially uniformly distributed over the entire piezoelectric plate 30, thus reducing or preventing the local excessive deformation of the piezoelectric plate 30 such as buckling or cracking, for example. As a result, damage to the piezoelectric plate 30 is reduced or prevented.

Also in such Preferred Embodiment 9, similar to Preferred Embodiment 2 described above, the vibration detection sensitivity may be increased in the bioacoustic sensor 824 including the piezoelectric plate 30.

The present invention has been described above with reference to a plurality of preferred embodiments including Preferred Embodiment 1 to Preferred Embodiment 9, but preferred embodiments of the present invention are not limited thereto.

For example, in the case of Preferred Embodiment 1 described above, as illustrated in FIG. 6, the piezoelectric plate support 32 being an annular body entirely surrounds the circumference of the vibration transmitter 34 being a columnar body, when viewed in the thickness direction (Z-axis direction). Further, in the case of Preferred Embodiment 2 described above, as illustrated in FIG. 10, the vibration transmitter 134 being an annular body entirely surrounds the circumference of the piezoelectric plate support 132 being a columnar body, when viewed in the thickness direction. However, the preferred embodiments of the present invention are not limited thereto.

For example, when viewed in the thickness direction of the piezoelectric plate, a plurality of (at least three) piezoelectric plate supports being columnar bodies may surround the vibration transmitter being a columnar body at regular intervals in a circumferential direction. Alternatively, when viewed in the thickness direction of the piezoelectric plate, a plurality of (at least three) vibration transmitters being columnar bodies may surround the piezoelectric plate support being a columnar body at regular intervals in a circumferential direction. Even in such cases, the piezoelectric plate may flexurally be deformed.

Further, in the case of Preferred Embodiment 1 described above, the diaphragm support 28 is made of a material that is elastically deformable in the thickness direction of the diaphragm 26, and is made of a sponge material, for example. However, the preferred embodiments of the present invention are not limited thereto. For example, the diaphragm support 28 may be a spring that expands and contracts in the thickness direction. That is, the diaphragm support may be a member or a mechanism that supports the diaphragm to be able to displace in the thickness direction thereof. For example, compressed air of an air spring may support the diaphragm. Furthermore, it is possible to omit the diaphragm support 28. For example, the diaphragm support 28 may be omitted when an inside diameter of the recessed portion 20b of the housing 20 is slightly larger than an outside diameter of the diaphragm 26, and the diaphragm 26 is able to reciprocate like a piston along an inner peripheral surface of the recessed portion 20b of the housing 20.

Furthermore, in the case of Preferred Embodiment 1 described above, the vibration transmitter 34 is fixed to both the diaphragm 26 and the piezoelectric plate 30 using an adhesive. However, the preferred embodiments of the present invention are not limited thereto. The vibration transmitter does not have to be fixed to the diaphragm and the piezoelectric plate, as long as the contact of the diaphragm and the piezoelectric plate with the vibration transmitter may be maintained. Further, in consideration of damage to the piezoelectric plate 30, it is preferable that the vibration transmitter 34 in contact with the center side portion of the first surface 30a of the piezoelectric plate 30 be fixed to the piezoelectric plate 30. Since the vibration of the diaphragm 26 causes stress to concentrate in the center side portion of the piezoelectric plate 30 as compared with other portions, specifically, compression deformation and tensile deformation occur repeatedly. Therefore, it is preferable that deformation rigidity of the center side portion of the piezoelectric plate 30 be increased by fixing the vibration transmitter 34. Note that, in the case above, the vibration transmitter 34 may integrally be provided to the piezoelectric plate 30 as a protruding portion, for example.

Furthermore, in the case of Preferred Embodiment 1 described above, the hardness of the piezoelectric plate 30 and the hardness of the vibration transmitter 34 are higher than the hardness of the piezoelectric plate support 32. However, the preferred embodiments of the present invention are not limited thereto. For example, the vibration transmitter 34 and the piezoelectric plate support 32 may have substantially the same hardness since both are made of the same material, for example. Further, for example, the hardness of the vibration transmitter 34 may be lower than the hardness of the piezoelectric plate support 32 as long as vibration can be transmitted from the diaphragm 26 to the piezoelectric plate 30. That is, any relationship in hardness between the piezoelectric plate 30, the piezoelectric plate support 32, and the vibration transmitter 34 is acceptable as long as the piezoelectric plate 30 may flexurally be deformed by the vibration of the diaphragm 26.

Furthermore, in the cases of Preferred Embodiment 1 to Preferred Embodiment 9 described above, the bioacoustic sensor is incorporated into a stethoscope. However, bioacoustic sensors of preferred embodiments of the present invention may be used in applications other than a stethoscope. For example, the bioacoustic sensor may be used as a heart sound sensor that remains worn on a living body for an extended period of time to continue monitoring a heart sound.

That is, a bioacoustic sensor according to an preferred embodiment of the present invention is, in a broad sense, a bioacoustic sensor that includes a housing, a diaphragm including a contact surface contactable with a living body and a back surface on an opposite side to the contact surface, and being displaceable in a thickness direction, and a piezoelectric plate including a first surface facing the back surface of the diaphragm with a gap therebetween and a second surface on an opposite side to the first surface to convert vibration of the diaphragm into an electric signal. The diaphragm is in contact with a center side portion of the first surface of the piezoelectric plate when viewed in the thickness direction, and the housing supports an outer side portion of the second surface of the piezoelectric plate when viewed in the thickness direction.

Further, a bioacoustic sensor according to another preferred embodiment of the present invention is, in a broad sense, a bioacoustic sensor that includes a housing, a diaphragm including a contact surface contactable with a living body and a back surface on an opposite side to the contact surface, and being displaceable in a thickness direction, and a piezoelectric plate including a first surface facing the back surface of the diaphragm with a gap therebetween and a second surface on an opposite side to the first surface to convert vibration of the diaphragm into an electric signal. The diaphragm is in contact with an outer side portion of the first surface of the piezoelectric plate when viewed in the thickness direction, and the housing supports a center side portion of the second surface of the piezoelectric plate when viewed in the thickness direction.

While the present invention has been described referencing a plurality of preferred embodiments, it will be apparent to those skilled in the art that at least one preferred embodiment combined in whole or in part with at least a portion of a preferred embodiment may provide further preferred embodiments according to the present invention.

Preferred embodiments of the present invention are applicable to devices for measuring a sound (vibration) generated in a living body such as a heart sound.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A bioacoustic sensor, comprising:
- a housing;
- a diaphragm including a contact surface contactable with a living body and a back surface on an opposite side to the contact surface, and being displaceable in a thickness direction;
- a piezoelectric plate including a first surface facing the back surface of the diaphragm with a gap between the first surface and the back surface and a second surface on an opposite side to the first surface to convert vibration of the diaphragm into an electric signal; and
- an elastically deformable piezoelectric plate support sandwiched between the piezoelectric plate and the housing to support the outer side portion of the second surface of the piezoelectric plate; wherein
- the diaphragm is in contact with a center side portion of the first surface of the piezoelectric plate when viewed in the thickness direction;
- the housing supports an outer side portion of the second surface of the piezoelectric plate when viewed in the thickness direction; and
- the housing indirectly supports the piezoelectric plate via the piezoelectric plate support.

2. The bioacoustic sensor according to claim 1, further comprising:
- a diaphragm support provided to the housing to support the diaphragm and being elastically deformable in the thickness direction.

3. The bioacoustic sensor according to claim 1,
- wherein a portion of the housing facing the second surface of the piezoelectric plate includes a concave surface, and the housing directly supports the outer side portion of the second surface of the piezoelectric plate via the concave surface.

4. The bioacoustic sensor according to claim 3, wherein a convex surface corresponding to the concave surface of the housing is provided to the back surface of the diaphragm; and the diaphragm is in direct contact with the piezoelectric plate via the convex surface.

5. The bioacoustic sensor according to claim 1, further comprising:

a vibration transmitter sandwiched between the diaphragm and the piezoelectric plate and in contact with the center side portion of the first surface of the piezoelectric plate to transmit vibration of the diaphragm to the piezoelectric plate;

wherein the diaphragm is in indirect contact with the piezoelectric plate via the vibration transmitter.

6. The bioacoustic sensor according to claim 5, wherein the piezoelectric plate support is made of an elastically deformable material.

7. The bioacoustic sensor according to claim 5, wherein the vibration transmitter includes a columnar body; and the piezoelectric plate support includes an annular body along an outer peripheral edge of the piezoelectric plate.

8. The bioacoustic sensor according to claim 5, wherein one end surface of the vibration transmitter is fixed to the back surface of the diaphragm.

9. The bioacoustic sensor according to claim 5, wherein another end surface of the vibration transmitter is fixed to the first surface of the piezoelectric plate.

10. The bioacoustic sensor according to claim 5, wherein the vibration transmitter has a lower hardness in an outer side portion than in a center side portion.

11. The bioacoustic sensor according to claim 5, wherein an end surface of the vibration transmitter on a side of the piezoelectric plate includes a rounded corner.

12. The bioacoustic sensor according to claim 5, further comprising:

a first damper between the diaphragm and the piezoelectric plate; and a second damper between the piezoelectric plate and the housing; wherein the first damper has a hardness lower than a hardness of the vibration transmitter; and the second damper has a hardness lower than a hardness of the piezoelectric plate support.

13. A stethoscope, comprising:

the bioacoustic sensor according to claim 1;

a speaker drivable based on an electric signal from the piezoelectric plate of the bioacoustic sensor;

a chest piece including the bioacoustic sensor and the speaker; and an ear chip connected to the chest piece to output a sound of the speaker to an outside.

14. The bioacoustic sensor according to claim 1, wherein the piezoelectric plate support includes an annular body along an outer peripheral edge of the piezoelectric plate.

15. A bioacoustic sensor, comprising:

a housing;

a diaphragm including a contact surface contactable with a living body and a back surface on an opposite side to the contact surface, and being displaceable in a thickness direction; and a piezoelectric plate including a first surface facing the back surface of the diaphragm with a gap between the first surface and the back surface and a second surface on an opposite side to the first surface to convert vibration of the diaphragm into an electric signal;

a vibration transmitter sandwiched between the diaphragm and the piezoelectric plate and in contact with the center side portion of the first surface of the piezoelectric plate to transmit vibration of the diaphragm to the piezoelectric plate; and a piezoelectric plate support sandwiched between the piezoelectric plate and the housing to support the outer side portion of the second surface of the piezoelectric plate; wherein the diaphragm is in contact with a center side portion of the first surface of the piezoelectric plate when viewed in the thickness direction;

the housing supports an outer side portion of the second surface of the piezoelectric plate when viewed in the thickness direction;

the diaphragm is in indirect contact with the piezoelectric plate via the vibration transmitter;

the housing indirectly supports the piezoelectric plate via the piezoelectric plate support; and a thickness of the piezoelectric plate support is a thickness with which a center of the second surface of the piezoelectric plate comes into contact with the housing when a predetermined force or more is applied to the diaphragm and the piezoelectric plate is flexurally deformed.

16. A bioacoustic sensor, comprising:

a housing;

a diaphragm including a contact surface contactable with a living body and a back surface on an opposite side to the contact surface, and being displaceable in a thickness direction; and a piezoelectric plate including a first surface facing the back surface of the diaphragm with a gap between the first surface and the back surface and a second surface on an opposite side to the first surface to convert vibration of the diaphragm into an electric signal;

a vibration transmitter sandwiched between the diaphragm and the piezoelectric plate and in contact with the center side portion of the first surface of the piezoelectric plate to transmit vibration of the diaphragm to the piezoelectric plate; and a piezoelectric plate support sandwiched between the piezoelectric plate and the housing to support the outer side portion of the second surface of the piezoelectric plate; wherein the diaphragm is in contact with a center side portion of the first surface of the piezoelectric plate when viewed in the thickness direction;

the housing supports an outer side portion of the second surface of the piezoelectric plate when viewed in the thickness direction;

the diaphragm is in indirect contact with the piezoelectric plate via the vibration transmitter;

the housing indirectly supports the piezoelectric plate via the piezoelectric plate support; and a thickness of the vibration transmitter is a thickness with which an outer peripheral edge of the first surface of the piezoelectric plate comes into contact with the diaphragm when a predetermined force or more is applied to the diaphragm and the piezoelectric plate is flexurally deformed.

* * * * *